US00PP14812P2

(12) United States Plant Patent
Hofmann

(10) Patent No.: US PP14,812 P2
(45) Date of Patent: May 25, 2004

(54) NEW GUINEA IMPATIENS PLANT NAMED 'FISNICS SALMON ICE'

(50) Latin Name: *Impatiens hawkeri*
Varietal Denomination: Fisnics Salmon Ice

(76) Inventor: Birgit Christa Hofmann, Gassenweg 29, 56170 Bendorf (DE)

( * ) Notice: Subject to any disclaimer, the term of this patent is extended or adjusted under 35 U.S.C. 154(b) by 17 days.

(21) Appl. No.: 10/452,984

(22) Filed: Jun. 3, 2003

(51) Int. Cl.[7] ..... A01H 5/00

(52) U.S. Cl. ..... Plt./318

(58) Field of Search ..... Plt./318

*Primary Examiner*—Kent L. Bell
(74) *Attorney, Agent, or Firm*—C. A. Whealy

(57) ABSTRACT

A new and distinct cultivar of New Guinea Impatiens plant named 'Fisnics Salmon Ice', characterized by its outwardly spreading and uniformly mounded plant habit; small to medium growth habit; freely branching and freely flowering habit; medium green-colored foliage; large, rounded, light red-colored flowers with white-colored centers; and flowers positioned above and beyond the foliage.

1 Drawing Sheet

Botanical classification/cultivar designation: *Impatiens hawkeri* cultivar Fisnics Salmon Ice.

BACKGROUND OF THE INVENTION

The present Invention relates to a new and distinct cultivar of New Guinea Impatiens plant, botanically known as *Impatiens hawkeri*, and hereinafter referred to by the name 'Fisnics Salmon Ice'.

The new Impatiens is a product of a planned breeding program conducted by the Inventor in Hillscheid, Germany and Galder, Gran Canaria, Spain. The objective of the breeding program is to develop new medium-sized Impatiens cultivars with an early to medium flowering response and large rounded flowers with attractive coloration.

The new Impatiens originated from a cross-pollination made by the Inventor during the spring of 1999 of the *Impatiens hawkeri* cultivar Fisnics Red, disclosed in U.S. Plant Pat. No. 13,226, as the female, or seed, parent with the *Impatiens hawkeri* cultivar Danharwt, not patented, as the male, or pollen, parent. The cultivar Fisnics Salmon Ice was discovered and selected by the Inventor as a flowering plant within the progeny of the stated cross-pollination in a controlled environment in Galder, Gran Canaria, Spain in April, 2000.

Asexual reproduction of the new cultivar by terminal cuttings taken in Galder, Gran Canaria, Spain, since July, 2000, has shown that the unique features of this new Impatiens are stable and reproduced true to type in successive generations.

SUMMARY OF THE INVENTION

The following traits have been repeatedly observed and are determined to be the unique characteristics of 'Fisnics Salmon Ice'. These characteristics in combination distinguish 'Fisnics Salmon Ice' as a new and distinct Impatiens cultivar:

1. Outwardly spreading and uniformly mounded plant habit; small to medium growth habit.
2. Freely branching and freely flowering habit.
3. Medium green-colored foliage.

4. Large, rounded, light red-colored flowers with white-colored centers; flowers positioned above and beyond the foliage.

Plants of the new Impatiens can be compared to plants of the female parent, the cultivar Fisnics Red. In side-by-side comparisons conducted by the Inventor in Hillscheid, Germany, plants of the new Impatiens differed from plants of the cultivar Fisnics Red in the following characteristics:

1. Plants of the new Impatiens were smaller than plants of the cultivar Fisnics Red.
2. Plants of the new Impatiens had larger flowers than plants of the cultivar Fisnics Red.
3. Flowers of plants of the new Impatiens were light red in color with white-colored centers whereas flowers of plants of the cultivar Fisnics Red were red in color.

Plants of the new Impatiens can be compared to plants of the male parent, the cultivar Danharwt. In side-by-side comparisons conducted by the Inventor in Hillscheid, Germany, plants of the new Impatiens differed primarily from plants of the cultivar Danharwt in flower color as plants of the cultivar Danharwt had white-colored flowers.

Plants of the new Impatiens can also be compared to plants of the cultivar BFP-650 Peach, disclosed in U.S. Plant Pat. No. 10,108. In side-by-side comparisons conducted by the Inventor in Hillscheid, Germany, plants of the new Impatiens differed from plants of the cultivar BFP-650 Peach in the following characteristics:

1. Plants of the new Impatiens were smaller than plants of the cultivar BFP-650 Peach.
2. Plants of the new Impatiens had lighter green-colored leaves than plants of the cultivar BFP-650 Peach.
3. Plants of the new Impatiens had larger flowers than plants of the cultivar BFP-650 Peach.
4. Flowers of plants of the new Impatiens and the cultivar BFP-650 Peach differed in flower coloration.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Impatiens. The photograph comprises a side perspective view of a typical flowering plant of 'Fisnics Salmon Ice' grown in a container.

DETAILED BOTANICAL DESCRIPTION

The cultivar Fisnics Salmon Ice has not been observed under all possible environmental conditions. The phenotype may vary somewhat with variations in environment such as temperature and light intensity, without, however, any variance in genotype.

The aforementioned photograph, following observations and measurements describe plants grown in Hillscheid, Germany, under commercial production practice in a glass-covered greenhouse. Rooted young plants were planted in 12-cm containers in late February and the aforementioned photograph and following observations and measurements were taken about 11 weeks later in early May. During the production of the plants, day temperatures were about 18 to 22° C. and night temperatures were about 16 to 18° C. In the following description, color references are made to The Royal Horticultural Society Colour Chart, 1995 Edition, except where general terms of ordinary dictionary significance are used.

Botanical classification: *Impatiens hawkeri* cultivar Fisnics Salmon Ice.

Parentage:

*Female parent.*—*Impatiens hawkeri* cultivar Fisnics Red, disclosed in U.S. Plant Pat. No. 13,226.

*Male parent.*—*Impatiens hawkeri* cultivar Danharwt, not patented.

Propagation:

*Type cutting.*—Terminal tip cuttings.

*Time to initiate roots.*—Summer: About 8 to 10 days at 24° C. Winter: About 12 to 15 days at 21° C.

*Time to produce a rooted cutting.*—Summer: About 15 days at 24° C. Winter: About 18 to 20 days at 21° C.

*Root description.*—Numerous, fibrous, and freely branching; 158D in color.

Plant description:

*General appearance.*—Outwardly spreading and uniformly mounded plant growth habit; small to medium growth habit; freely branching habit, dense and bushy appearance; freely flowering. Moderately vigorous.

*Crop time.*—From a rooted cutting, about 9 to 10 weeks are required to produce finished flowering plants in 12-cm containers.

*Plant height.*—About 19.5 cm.

*Plant diameter or spread.*—About 35 cm.

*Lateral branches.*—Quantity per plant: About 8 to 10. Length: About 15 to 17 cm. Diameter: About 5 to 6 mm. Internode length: About 3.5 to 4 cm. Texture: Smooth, glabrous. Color: 145C; towards the nodes, faintly overlain with 179B.

*Foliage description.*—Arrangement: Primarily in whorls. Length: About 12 to 13 cm. Width: About 3 to 4 cm. Shape: Elliptic. Apex: Acute to acuminate. Base: Acute. Margin: Serrulate with ciliation. Texture: Smooth, slightly rugose; glabrous. Color: Developing foliage, upper surface: 143A. Developing foliage, lower surface: 139C. Fully expanded foliage, upper surface: 137A. Fully expanded foliage, lower surface: 139C. Venation, upper surface: 145A. Venation, lower surface: 143D. Petiole: Length: About 1 to 1.5 cm. Diameter: About 4 mm. Texture: Smooth, glabrous. Color, upper surface: 48B. Color, lower surface: 179C.

Flower description:

*Flower type and flowering habit.*—Single, rounded, large, light red-colored flowers with white-colored centers. Freely and continuously flowering; usually about 6 to 8 flowers and flower buds per lateral branch. Flowers positioned above and beyond the foliage; flowers typically face parallel to the leaf canopy. Petals not persistent; gynoecium persistent. Flowers not fragrant.

*Flower longevity.*—Flowers last about 8 to 9 days on the plant.

*Flowering season.*—Year-round under greenhouse conditions. Plants begin flowering about 9 weeks after planting.

*Flower buds.*—Length: About 2.2 cm. Diameter: About 1.7 cm. Shape: Ovoid. Color: 43C.

*Flower length.*—About 7. 4 to 7.6 cm.

*Flower width.*—About 7.4 to 7.6 cm.

*Flower depth.*—About 1 to 1.5 cm.

*Petals.*—Quantity: Five per flower, imbricate. Length: Banner petals: About 3 to 3.2 cm. Lateral petals: About 3.5 to 3.7 cm. Base petals: About 4 to 4.2 cm. Width: Banner petal: About 4.2 to 4.4 cm. Lateral petals: About 3.2 cm. Base petals: About 3.8 to 4 cm. Shape: Cordate. Apex: Moderately lobed, emarginate. Base: Attenuate. Margin: Entire. Aspect: Flat to slightly cupped. Texture: Smooth; satiny. Color: When opening, upper surface: 40A. When opening, lower surface: 43C. Fully opened, upper surface: 43C; towards the base, 155D; eye zone, 68C. Color becoming closer to 43D with development. Fully opened, lower surface: 43C to 43D.

*Spur.*—Quantity: One per flower. Length: About 5.5 to 6 cm. Diameter: At apex: About 0.5 mm. At flower: About 3 mm. Aspect: Curved. Color: 52B to 52C.

*Peduncles.*—Length: About 5 cm. Diameter: About 2 mm. Texture: Smooth, glabrous. Strength: Strong, flexible. Color: 144C; towards the base, 179B.

*Reproductive organs.*—Androecium: Stamen number: Five fused at anthers, hooded; filaments free. Anther length: About 5 mm. Anther shape: Obovate. Anther color: 43C. Pollen amount: Moderate. Pollen color: 8D. Gynoecium: Pistil quantity: One per flower. Pistil length: About 7 mm. Stigma color: 8D. Style color: 8D. Ovary: Five-celled. Ovary color: 143A.

*Seed/fruit.*—Feed and fruit development has not been observed.

Disease/pest resistance: Plants of the new Impatiens have not been observed to be resistant to pathogens and pests common to Impatiens.

Low temperature tolerance: Plants of the new Impatiens have been observed to tolerate night temperatures of 5° C. with 10° C. day temperatures.

It is claimed:

1. A new and distinct cultivar of New Guinea Impatiens plant named 'Fisnics Salmon Ice', as illustrated and described.

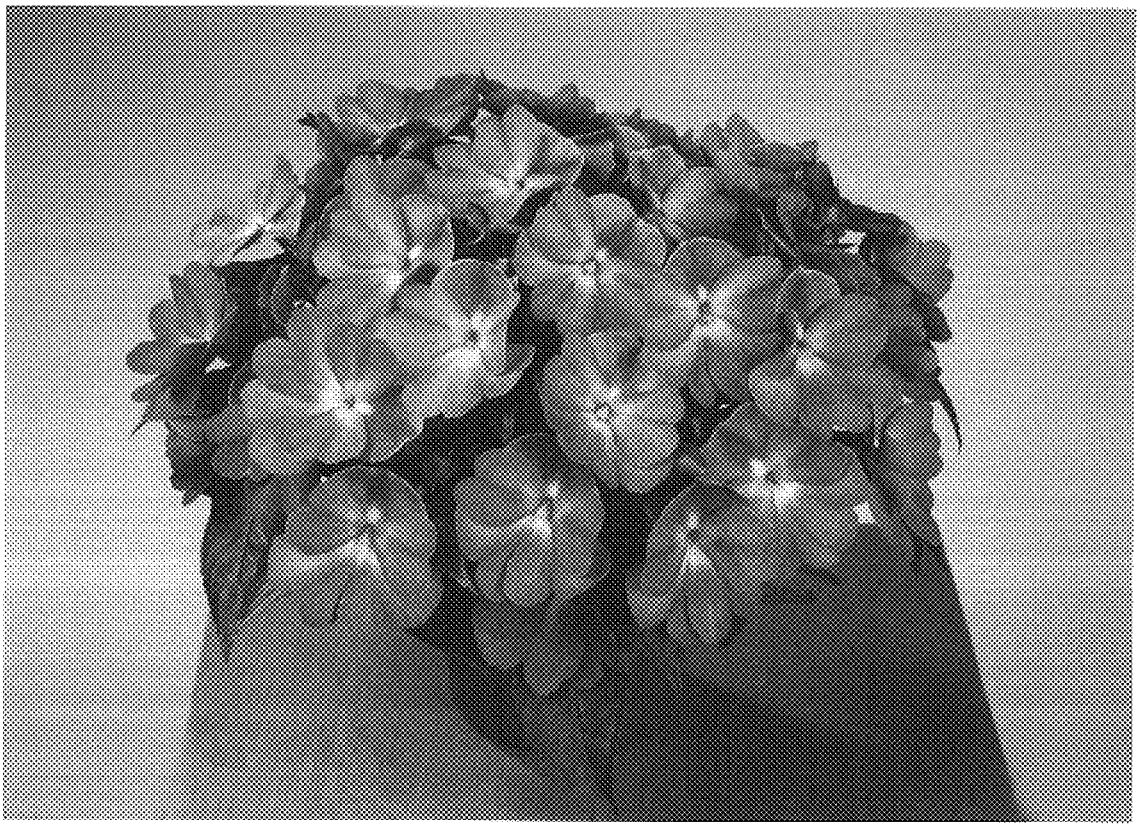

* * * * *